United States Patent [19]

Wilde

[11] Patent Number: 4,937,261
[45] Date of Patent: Jun. 26, 1990

[54] FUNGICIDAL COMPOSITION WITH SYNERGISTIC ACTIVITY

[75] Inventor: Thomas Wilde, Berlin, Fed. Rep. of Germany

[73] Assignee: Schering Aktiengesellschaft, Fed. Rep. of Germany

[21] Appl. No.: 287,902

[22] Filed: Dec. 21, 1988

[30] Foreign Application Priority Data

Dec. 21, 1987 [DE] Fed. Rep. of Germany ....... 3744053

[51] Int. Cl.⁵ .............................................. A01N 47/10
[52] U.S. Cl. ..................................... 514/479; 514/491
[58] Field of Search ................................. 514/479, 491

[56] References Cited

U.S. PATENT DOCUMENTS

4,474,805 10/1984 Lorusso et al. ...................... 514/479

FOREIGN PATENT DOCUMENTS

0004357 10/1979 European Pat. Off. ............ 514/479
0040007 5/1983 European Pat. Off. .
0106558 7/1987 European Pat. Off. .

*Primary Examiner*—Allen J. Robinson
*Attorney, Agent, or Firm*—Ostrolenk, Faber, Gerb & Soffen

[57] ABSTRACT

There is described a fungicidal composition which comprises a synergistic amount of
  (a) propyl 3-(dimethylamino)propylcarbamate or an acid addition salt thereof, and
  (b) a compound selected from the group consisting of zinc propylenebis(dithiocarbamate) polymer (propineb), zinc ethylenebis(dithiocarbamate) polymer (zineb), manganese ethylenebis(dithiocarbamate) polymer (maneb), zinc ammoniate ethylenebis(dithiocarbamate)-poly(ethylenethiuramdisulphide) (metiram), tetrachloroisophthalonitrile (chlorothalonil) and copper(I)oxide, as well as carriers and/or other additives, the ratio of component A to component B being preferably from about 1:0.1-3.

9 Claims, No Drawings

FUNGICIDAL COMPOSITION WITH SYNERGISTIC ACTIVITY

This invention relates to a fungicidal composition with synergistic activity.

The composition contains, as essential ingredients, two components that mutually affect each other when used together and display a biological activity that is greater than the sum of the activities when used alone, an effect which is designated as synergism. This synergism leads to an increased protective activity when treating plants against a large number of fungi.

Thus these fungicidal compositions can be used in plant protection for combating Deuteromycetes, Zygomycetes, Basidiomycetes, Plasmodiophoraceae, Ascomycetes, Domycetes and Chytridiomycetes.

Compositions with fungicidal activity are already known and are the subject of Patents such as for example DE OS No. 6 05 551. Mixtures of fungicides that show a synergisitic activity are known (EP No. 106558 and 40007). However, there is still a considerable need and in even greater amounts for further compositions in this area with increased activity in order especially to meet the increased demands for protection of the environment and to overcome resistance.

The object of the present invention is thus to provide a fungicidal composition with synergistic activity. This object is provided according to the invention, by a composition that is characterised by a content of
  (a) propyl 3-(dimethylamino)propylcarbamate or an acid addition salt thereof, and
  (b) a compound selected from the group consisting of zinc propylenebis(dithiocarbamate) polymer (propineb), zinc ethylenebis(dithiocarbamate) polymer (zineb). manganese ethylenebis(dithiocarbamate) polymer (maneb), zinc ammoniate ethylenebis(dithiocarbamate) poly(ethylenethiuramdisulphide) (metiram), tetrachloro isophthalonitrile (chlorothalonil) and copper(I)oxide, as well as carriers an other additives.

the ratio of component A to component B being preferably from about 1:0.1-3.

Component A can be used in the form of an acid addition salt as well as its free base. The salts can be derived from inorganic or organic acids, such as mineral acids. mono or polycarboxylic acids or sulphonic acids for example: hydrochloric acid, sulphuric acid, formic acid, propionic acid, valeric acid, oxalic acid, malonic acid, succinic acid, cyanoacetic acid, chloroacetic acid, dichloroacetic acid, trifluoroacetic acid, benzoic acid, furan-2-carboxylic acid, p-toluenesulphonic acid, methanesulphonic acid, thioglycolic acid and citric acid.

The compositions of the invention show a surprising fungicidal activity that exceeds the sum of the activities of the individual components when used alone. This synergistic activity could not be envisaged from the present state of knowledge.

The synergistic activity of the composition of the invention is significantly displayed in a mixture ratio of 1 part by weight of component A to 0.1 to 3 parts by weight of component B, although these limits can be exceeded by greater or smaller amounts by weight. The composition of the invention shows increased activity in comparison to the additive activity of the individual components if one part by weight of propamocarb (component A) is used in the mixture with:

0.5-1.5 parts by weight propineb
1.0-3.0 parts by weight zineb
0.5-1.5 parts by weight maneb
0.5-2.0 parts by weight metiram
0.5-2.0 parts by weight chlorothalonil
or 1.0-3.0 parts by weight copper(I)oxide
as component B.

However, the weight ratio of component A and B depends on the sensitivity and resistance of the plants, the time of application the climatic conditions and the soil conditions.

The composition of the invention shows a wide fungicidal activity against fungi of various systematic types, such as: Aphanomyces; Bremia; Peronospora: Phytophthora; e.g. *Phytophthora infestans*; Pseudoperonospora, e.g. *Pseudoperonospora humuli*; Pythium and Plasmopara e.g. *Plasmopara viticola*.

In treating parts of the plant above the ground, protection is given against wind-borne diseases. In order to protect against seed-borne diseases the compounds of the invention can be used as a seed treatment. Besides they also act systemically, that means they are taken up by the roots of the plant, for example after sowing, are transported into the parts of the plant above the earth and protect against these diseases Because of the broad spectrum of activity that has been found, the compositions are suitable not only for protection of crops, but also for protection of materials and for combating microbes which are Pathogenic to humans and animals from which wide-ranging possibilities of use arise.

The rate of use lies as a rule from 500 to 9000 g of the mixture (components A and B)/ha, preferably 1700 to 3500 g mixture/ha.

The composition can be applied in conventional manner, for example with water as carrier in spray amounts of about 100 to 2000 liters per hectare. Application of the composition by so-called "low-volume" or "ultra-low volume" methods is also possible.

The composition of the invention can be used also in mixture with each other active ingredients, for example growth regulants. Plant nutrients, soil-structure improvers, defoliants, plant-protection agents or pesticides, depending on the desired result.

An improvement in the intensity and speed of action can be obtained, for example, by addition of suitable adjuvants, such as organic solvents, wetting agents and oils. Such additives may allow a decrease in the dose.

The compositions of the invention can suitably be used as powders, dusts, granules, solutions, emulsions or suspensions, with the addition of liquid and/or solid carriers and/or diluents and, optionally, binding, wetting, emulsifying and/or dispersing adjuvants.

Suitable liquid carriers are, for example water, aliphatic and aromatic hydrocarbons such as benzene, toluene and xylene, cyclohexanone, isophorone, dimethyl sulphoxide, dimethylformamide and other mineral-oil fractions.

Suitable solid carriers include mineral earths, e.g. tonsil, silica gel, talcum, kaolin, attapulgite, limestone, silicic acid and plant products. e.g. flours.

As surface-active agents there can be used for example calcium lignosulphonate. Polyoxyethylenealkylphenyl ether, naphthalenesulphonic acids and their salts, phenolsulphonic acids and their salts, formaldehyde condensates, fatty alcohol sulphates, as well as substituted benzenesulphonic acids and their salts.

The amount of the mixture (components A and B) in the composition of the invention in the various preparations can vary over a wide range. For example the compostion can contain around 10 to 80 weight percent of the mixture, around 90 to 20 weight percent of liquid or solid carriers, as well as optionally up to 20 weight percent of surfactant.

Formulations can be prepared, for example, from the following ingredients.

(a) 90% mixture (components A+B)
7% kaolin
3% surfactant based on the sodium salt of N-methyl-N-oleyltaurine and calcium lignosulphonate (b)
50% mixture (components A+B)
35% colloidal silicic acid
10% calcium lignosulphonate
5% ammonium tetraethyleneglycolnonyl phenyl monosulphate (c)
30% mixture (components A+B)
2% colloidal silicic acid
6% water (d)
20% mixture (components A+B)
70% tonsil
8% cell pitch
2% wetting agent based on fatty acid condensation products (e)
5% mixture (components A+B)
80% tonsilite
10 cell pitch
5% wetting agent based on fatty acid condensation products The preparation of the composition of the invention can be carried out by mixing the individual components in a suitable apparatus for this purpose.

The following examples illustrate the possibility of use of the compositions of the invention.

The examples contain data on components A and B, their rates of use, the percentage fungicidal acitivity achieved and the percentage inhibition obtained with the combination of A and B according to the method described by S. R. Colby, in which the existence of additive activity would be expected (S. R. Colby "Calculating Synergistic and Antagonistic Respones of Herbicide Combinations" Weeds 15/1 (1967) P 22-22).

The calculation was carried out according to the following equation:

$$E = X + Y - \frac{XY}{100}$$

in which
X=the percentage of fungicidal activity with substance A at P kg active ingredient/ha
Y=the percentage of fungicidal activity with substance B at g kg active ingredient/ha
E=expected fungicidal activity by A+B at P+q kg/ha.

If the observed value is higher than the value E calculated according to Colby, the combination has a synergistic activity.

TEST EXAMPLE

Testing of the composition of the invention against phytophthora infestans in field tests on potatoes ("Bintje") in test areas of ca. 20 m² (four replicates).

Preparations of active ingredients were formulated with water to the desired concentration using commercially available formulations of the ingredients, The plants were sprayed at a spray interval of 7-12 days with the preparations of active ingredients. The evaluation was carried out 12 days after the last treatment (infestation of the untreated controls was 100%).

| Rate of application (g a·i/ha) | | % Activity | | |
|---|---|---|---|---|
| propamocarb HCl | maneb | Observed | Calculated (E) | Trial site |
| 1125 | 0 | 9.5 | | |
| 0 | 1200 | 8.7 | | I |
| 1125 | 1200 | 32.5 | 17.4 | |

In a similar manner the following results were obtained.

| Rate of application (g a·i/ha) | | % Activity | | |
|---|---|---|---|---|
| propamocarb HCl | propineb | Observed | Calculated (E) | Trial site |
| 1125 | 0 | 9.5 | | |
| 0 | 1050 | 1.0 | | I |
| 1125 | 1050 | 22.5 | 10.4 | |
| propamocarb HCl | metiram | Observed | Calculated (E) | Trial site |
| 1125 | 0 | 9.5 | | |
| 0 | 1200 | 1.2 | | I |
| 1125 | 1200 | 28.7 | 10.6 | |
| propamocarb base | zineb | Observed | Calculated (E) | Trial site |
| 1125 | 0 | 67.7 | | |
| 0 | 2000 | 77.2 | | I |
| 1125 | 2000 | 95.1 | 92.6 | |
| 1125 | 0 | 51.3 | | |
| 0 | 2000 | 54.6 | | II |
| 1125 | 2000 | 87.4 | 77.9 | |

| Rate of application (g a·i/ha) | | % Activity | | |
|---|---|---|---|---|
| propamocarb base | chloro-thalonil | Observed | Calculated (E) | Trial site |
| 1125 | 0 | 67.7 | | |
| 0 | 1300 | 82.3 | | I |
| 1125 | 1300 | 95.6 | 94.3 | |
| 1125 | 0 | 51.3 | | |
| 0 | 1300 | 66.7 | | II |
| 1125 | 1300 | 86.2 | 83.8 | |
| propamocarb base | copper (I) oxide | Observed | Calculated (E) | Trial site |
| 1125 | 0 | 67.7 | | |
| 0 | 2250 | 82.8 | | I |
| 1125 | 2250 | 97.0 | 94.4 | |
| 1125 | 0 | 51.3 | | |
| 0 | 2250 | 64.4 | | II |
| 1125 | 2250 | 91.3 | 82.7 | |

I claim:
1. A fungicidal composition comprising a synergistic fungicidally effective amount of the mixture of
(a) propyl 3-(dimethylamino)propylcarbamate or an acid addition salt thereof, and
(b) a compound selected from the group consisting of zinc propylenebis(dithiocarbamate) (propineb).

zinc ethylenebis(dithiocarbamate) (zineb), manganese ethylenebis(dithiocarbamate) (maneb) zinc ammoniate ethylenebis(dithiocarbamate)-poly(ethylenethiuramdisulphide) (metiram), and a carrier, wherein the ratio of component A to component B is from about 1:01.1 to 3.

2. The composition according to claim 1, wherein component B is propineb, the ratio of component A to component B is from about 1:0.5-1.5.

3. The composition according to claim 1 wherein component B is zineb, the ratio of component A to component B is from about 1:1.0-3.0.

4. The composition according to claim 1 wherein component B is maneb the ratio of component A to component B is from about 1:0.5-1.5.

5. A composition according to claim 1 wherein component B is metiram, the ratio of component A to component B is from about 1:0.5-1.5.

6. The composition according to claim 1 wherein component B is maneb.

7. A method of combating a fungus which comprises applying to the fungus or its locus a synergistic fungicidally effective amount of a mixture of
   (a) propyl 3-(dimethylamino)propylcarbamate or an acid addition salt thereof, and
   (b) a compound selected from the group consisting of zinc propylenebis(dithiocarbamate) polymer (propineb). zinc ethylenebis(dithiocarbamate) polymer (zineb). manganese ethylenebis(dithiocarbamate)-poly(ethylenethiuramdisulphide) zinc ammoniate (metiram), wherein the ratio of component A to component B is from about 1.0.1 to 3.

8. The method according to claim 7 wherein component B is maneb.

9. The method according to claim 8 wherein the ratio of component A to component B is from about 1:0.5 to 1.5.

* * * * *